United States Patent
Lang

(10) Patent No.: US 6,428,502 B1
(45) Date of Patent: Aug. 6, 2002

(54) PUNCTAL CANNULA

(75) Inventor: John C. Lang, Arlington, TX (US)

(73) Assignee: Alcon Manufacturing, Ltd., Fort Worth, TX (US)

(*) Notice: Subject to any disclaimer, the term of this patent is extended or adjusted under 35 U.S.C. 154(b) by 0 days.

(21) Appl. No.: 09/567,175

(22) Filed: May 8, 2000

Related U.S. Application Data

(60) Provisional application No. 60/141,199, filed on Jun. 25, 1999.

(51) Int. Cl.$^7$ .......................... A61M 25/00; A61M 5/32
(52) U.S. Cl. ................ 604/28; 604/264; 604/278; 604/290; 604/294; 604/513; 604/514
(58) Field of Search .................... 604/264, 28, 513, 604/514, 117, 278, 290, 294

(56) References Cited

U.S. PATENT DOCUMENTS

| | | | |
|---|---|---|---|
| 3,540,447 A | 11/1970 | Howe | 128/221 |
| 3,949,750 A | 4/1976 | Freeman | |
| 4,335,718 A | 6/1982 | Calabrese | 128/218 N |
| 4,915,684 A | 4/1990 | MacKeen et al. | 604/8 |
| 5,171,270 A | 12/1992 | Herrick | 623/11 |
| 5,283,063 A | 2/1994 | Freeman | 424/427 |
| 5,469,867 A | * 11/1995 | Schmitt | 128/898 |
| 5,499,065 A | 3/1996 | Zimmerman | 351/200 |
| 5,593,393 A | 1/1997 | Trudell et al. | 604/264 |
| 5,723,005 A | 3/1998 | Herrick | 623/4 |
| 5,826,584 A | * 10/1998 | Schmitt | 128/898 |

OTHER PUBLICATIONS

Grieshaber "Instruments for Irrigation Aspiration" Brochure, Feb. 1997, 1 page.

Alcon 1997–1998 Catalog, "Cutting Instruments, Cannulas & Cystitomes, Ophthalmic Sponges, OPTEMP Cautery", pp. 11–17.

Katena Eye Instruments Catalog Supplement; 1997, pp. 87, 92.

Storz Instruments for Optometry Brochure, Sortz Ophthalmics, 1993, 11 pp.

* cited by examiner

Primary Examiner—Gregory L. Huson
Assistant Examiner—Kathleen J. Prunner
(74) Attorney, Agent, or Firm—W. David Lee

(57) ABSTRACT

A lacrimal cannula, which is used for the removal of plugs or obstructions from mammalian lacrimal canaliculi having a punctum, includes a body having a distal portion, a proximal portion, an external annulus disposed proximate the distal portion, and a hollow bore for fluid delivery from the distal portion. The external annulus has an outer diameter greater than the outer diameter of the distal portion. The distal portion is inserted into the mammalian punctum without dilating the punctum and the external annulus has a generally spherical geometry which forms a seal with the external surface of the punctum without dilating the punctum and without the necessity of forcefully pressing the cannula against the punctal tissue to create a seal. The distal portion also has a relatively short length so that the distal portion is easily inserted into the canaliculus without contacting the plug or obstruction and thus interfering with the formation of the punctal seal. The proximal portion is coupled to a hub for removably coupling the proximal portion to a conventional syringe. Once the external surface of the punctum is sealed, the cannula is then used to inject an ophthalmic fluid, which may or may not be heated, into the punctum so as to pressurize a portion of the canaliculus between the plug or obstruction and the punctum to dislodge the plug or obstruction.

48 Claims, 6 Drawing Sheets

PUNCTAL CANNULA

This application claims the benefit of U.S. Provisional Application Serial No. 60/141,199, filed Jun. 25, 1999.

FIELD OF THE INVENTION

The present invention generally pertains to cannulas. More particularly, but not by way of limitation, the present invention pertains to cannulas for the removal of punctal plugs that are often used to treat dry eye syndrome, and to cannulas for the removal of obstructions from the lacrimal canaliculi.

DESCRIPTION OF THE RELATED ART

FIG. 1 illustrates the lacrimal duct system of a mammalian eye 10. The system includes a lower punctum 12 connected to a lower lacrimal canaliculus 14, and an upper punctum 16 connected to an upper lacrimal canaliculus 18. Canaliculi 14 and 18 are connected to a lacrimal sac 20 and a nasolacrimal duct 22. A lacrimal gland 24 is connected to eye 10 via a lacrimal duct 26. In general, tears are produced by lacrimal gland 24 and are provided to eye 10 via lacrimal duct 26, and tears are drained from eye 10 via punctum 12 and canaliculus 14, punctum 16 and canaliculus 18, and nasolacrimal duct 22.

By way of background, tears produced by lacrimal gland 24 are actually a complex composition in the form of a tear film. This tear film includes three basic layers: an outer lipid layer, an inner mucin layer, and an aqueous layer between the lipid and mucin layers. Each of the layers has a particular function. The lipid layer prevents evaporation of the tears from the surface of eye 10. The aqueous layer provides oxygen to the cornea and contains additional chemical components that are important to a healthy eye 10. The mucin layer provides for interaction between the lipid layer and the aqueous layer and prevents tears from "beading up" on the cornea.

Approximately 7.5 million cases of moderate or severe dry eye syndrome occur in the United States each year. An additional five million people are unable to wear contact lenses because of insufficient amounts of tear fluid. A "dry eye" is one that experiences insufficient lubrication of the cornea as a result a disturbance in the normal tear film. The condition encompasses a wide variety of disease states ranging from mild, intermittent burning and/or scratchiness with foreign body sensation, to a severe lack of aqueous layer secretion accompanied by corneal and conjunctival disease (keratoconjunctivitis sicca (KCS)). Dry eye can have a variety of specific causes and contributing factors, including arid environments, environmental airborne pollutants, certain systemic medications, auto-immune disorders, drug toxicity, hormone deficiency or changes, and even contact lens wear. However, the majority of cases of dry eye syndrome are related to two basic causes. First, lacrimal duct 26 from lacrimal gland 24 may become clogged or may malfunction so that an insufficient amount of tears reach eye 10. In response to this cause, artificial tear products such as TEARS NATURALE® and BION® TEARS, sold by Alcon® Laboratories, Inc. of Fort Worth, Tex., were developed. Second, although lacrimal gland 24 and lacrimal duct 26 may deliver a sufficient amount of tears to eye 10, tears may be drained away from eye 10 too quickly, creating a dry eye situation. In response to this cause, various methods and apparatus for sealing puncta 12 and 16 have been developed.

Initially, puncta 12 and 16 were sealed by stitching or by electrical or laser cauterization. Although such procedures can provide acceptable results, they are not reversible without reconstructive surgery. As it is sometimes difficult to determine whether dry eye is caused by too great of drainage or too little tear production, such procedures may expose the patient to unnecessary trauma. In addition, such procedures may result in epiphera, a condition where tears continually form on eye 10, build up, and run down the face of the patient.

Pre-formed collagen plugs for insertion into puncta 12 and 16 or the canaliculi 14 and 18 were developed to provide a reversible sealing procedure. Collagen plugs are water-soluble and, when inserted into the puncta, typically dissolve within seven to fourteen days. Collagen plugs are thus effective as a test procedure to determine if it is desirable to more permanently seal the puncta.

Pre-formed water-insoluble plugs for insertion into puncta 12 and 16 or canaliculi 14 and 18 are described in a variety of United States Patents. For example, U.S. Pat. No. 3,949,750 to Freeman describes such a plug having a head portion that extends outside of the punctum and a barb portion that extends into the punctum and/or canaliculus. Such plugs can be seen in the corner of eye 10, are sometimes uncomfortable, and are easily dislodged. In addition, such plugs are somewhat difficult to insert, and occasionally their size and shape causes tissue damage during insertion. If such plugs protrude too far from the puncta, they can cause irritation to the sclera. Furthermore, the tissue of the punctum can be damaged due to prolonged dilation caused by such plugs. U.S. Pat. No. 5,283,063 to Freeman describes a similar plug made from a hydrogel material having a hydrating port located in its barb portion that allows canalicular fluid to enter the barb and hydrate the plug to an expanded, relatively flexible state. U.S. Pat. Nos. 5,723,005 and 5,171,270 to Herrick describe water-insoluble punctal plugs that have collapsible flared sections for improved sealing and anchoring within the canaliculus. Some of these plugs also have a retaining portion that extends outside the punctum to further anchor the plug and prevent migration down the canaliculus. U.S. Pat. Nos. 3,949,750; 5,283,063; 5,723,005; and 5,171,270 are each incorporated herein by reference.

In addition, U.S. Pat. No. 5,469,867 to Schmitt describes a method of occluding the lacrimal canaliculi and other mammalian channels or ducts by injecting a heated, flowable polymer or polymer composite of a specified composition through puncta 12 and 16 into canaliculi 14 and 18, respectively. The specified polymer and polymer composite are non-immunogenic, biocompatible materials that are solid and/or non-flowable at body temperature or lower and flowable when heated slightly above body temperature. The polymer and polymer composite are capable of quickly changing from a flowable state to a non-flowable state by moving through only a few centigrade degrees of temperature. After injection, the polymer or polymer composite cools and solidifies to form a plug that conforms exactly to the geometry of the canaliculi. U.S. Pat. No. 5,469,867 is incorporated herein by reference, and the plugs for occluding the canaliculus or other mammalian channels disclosed therein will be referred to in this document as "cast-in place thermoplastic plugs".

As mentioned above, it is highly desirable that a punctal plug be removable without the necessity of surgery. Various conventional techniques have been utilized to remove the above-described water insoluble plugs. For example, such plugs that have a portion extending outside the punctum are typically removed using forceps or a similar instrument.

As another example, certain cannulas have been used to "flush" water-insoluble plugs not having a portion extending outside the punctum down nasolacrimal duct 22. More specifically, it is known to use a cannula having an outer diameter equal to or slightly greater than the diameter of punctum 12 to seal the punctum and then inject saline into the punctum. The seal is created by dilating the punctum with the cannula and the sphincter action of the punctal muscle tightening around the cannula. Saline is then injected into canaliculus 14 so as to create enough water pressure to flush the plug down nasolacrimal duct 22. An example of a conventional cannula that has been utilized to perform this technique is the E4404 lacrimal cannula sold by STORZ Ophthalmics of St. Louis, Mo., which has a 23 gauge outer diameter, 10 mm long tip.

It is also known to use a cannula having a smaller outer diameter distal tip (e.g. 26–27 gauge) that tapers into a larger outer diameter proximal portion (e.g. 23 gauge or greater) to perform a similar flushing procedure, such as the cannula disclosed in U.S. Pat. No. 5,593,393 to Trudell et al. When such a cannula is inserted into punctum 12 beyond the taper, the larger outer diameter proximal portion dilates punctum 12, and the sphincter action of the punctal muscle tightens around the proximal portion to complete the seal. Saline is then injected into canaliculus 14 so as to create enough water pressure to flush the plug down nasolacrimal duct 22.

However, dilation of the punctum can be dangerous, and prolonged dilation of the punctum can damage punctal tissue. In addition, due to the difference in sizes of a particular patient's punctum, such as, by way of example, the difference between a male adult human being, a female adult human being, and a child human being, cannulas with various outer diameters may be required to effectively create the above-described punctal seals.

Finally, it is known to use a cannula with an outer diameter less than the diameter of punctum 12 (e.g. 27 gauge) to flush such water-insoluble plugs down nasolacrimal duct 22. Such a cannula can be inserted into punctum 12 without dilation, but does not seal the punctum. Saline is then injected into canaliculus 14 in an attempt to create enough water pressure to flush the plug down nasolacrimal duct 22. However, such a cannula typically does not create enough water pressure to flush the plug due to the lack of a punctal seal, and excess saline is "backflushed" out of the eye and down the patient's face.

U.S. Pat. No. 5,469,867 discloses several techniques for removing its cast-in place thermoplastic plug from canaliculus 14. The plug may be physically extracted from the canaliculus by forceps or a similar instrument, or the plug may be heated by application of an electrical heating device that melts the polymer. In addition, a lipophilic compound such as a naturally occurring oil or fatty acid ester that dissolves into the polymer and reduces the melting point of the polymer below body temperature may be introduced into canaliculus 14 for plug removal. This technique transforms the plug into a flowable fluid that is removable by irrigation with saline solution, which is typically performed using one of the above-described cannulas.

Therefore, a need exists in the ophthalmic industry for an improved cannula for the removal of punctal plugs that are used to treat dry eye syndrome, and for the removal of obstructions from the lacrimal canaliculi, that does not suffer from the above-described problems. The improved cannula must be easy to use, safe for the patient, and capable of economic manufacture.

SUMMARY OF THE INVENTION

The present invention pertains to improved punctal cannula and methods of using such cannula to remove plugs or obstructions from mammalian canaliculi. More particularly, one aspect of the present invention comprises a cannula including a body having a distal portion, an external annulus disposed proximate the distal portion, and a hollow bore for fluid delivery from the distal portion. The distal portion is capable of insertion into a mammalian punctum without dilating the punctum. The external annulus has geometry capable of forming a seal with an external surface of the punctum without dilating the punctum.

In another aspect, the present invention comprises a method of dislodging a plug or an obstruction from a mammalian canaliculus having a punctum. A cannula including a body having a distal portion, an external annulus disposed proximate the distal portion, and a hollow bore for fluid delivery from the distal portion is provided. The distal portion is inserted into the punctum without dilating the punctum. The punctum is sealed by contacting an external surface of the punctum with the external annulus without dilating the punctum. An ophthalmic fluid is injected into the punctum with the cannula to pressurize a portion of the canaliculus between the plug or obstruction and the punctum.

In another aspect, the present invention comprises a lacrimal cannula including a body having a distal portion, an external annulus, and a hollow bore for fluid delivery from the distal portion. The external annulus has a generally spherical geometry with the distal portion extending axially therefrom. The distal portion is capable of insertion into a mammalian lacrimal punctum without dilating the punctum. The external annulus is capable of forming a seal with an external surface of the punctum without dilating the punctum.

In another aspect, the present invention comprises a lacrimal cannula including a body having a distal portion, an external annulus, and a hollow bore for fluid delivery from the distal portion. The external annulus has a generally inverted-cone shape geometry with the distal portion extending axially from a tip toward a base of the cone. The distal portion is capable of insertion into a mammalian lacrimal punctum without dilating the punctum. The external annulus is capable of forming a seal with an external surface of the punctum without dilating the punctum.

In another aspect, the present invention comprises a lacrimal cannula including a body having a distal portion, an external annulus, and a hollow bore for fluid delivery from the distal portion. The external annulus has a generally cone shape geometry with the distal portion extending axially and outwardly from a tip of the cone. The distal portion is capable of insertion into a mammalian lacrimal punctum without dilating the punctum. The external annulus is capable of forming a seal with an external surface of the punctum without dilating the punctum.

In a further aspect, the present invention comprises a method of removing a cast-in place thermoplastic plug from a mammalian lacrimal canaliculus having a punctum. A cannula including a body having a distal portion, an external annulus, and a hollow bore for fluid delivery from the distal portion is provided. The distal portion extends axially from the external annulus. The distal portion is inserted into the punctum without dilating the punctum. The punctum is sealed by contacting an external surface of the punctum with the external annulus without dilating the punctum. A warm ophthalmic fluid is injected into the punctum with the cannula to pressurize a portion of the canaliculus between the cast-in place thermoplastic plug and the punctum to dislodge the plug.

BRIEF DESCRIPTION OF THE DRAWINGS

For a more complete understanding of the present invention, and for further objects and advantages thereof, reference is made to the following description taken in conjunction with the accompanying drawings in which.

DETAILED DESCRIPTION OF PREFERRED EMBODIMENTS

The preferred embodiments of the present invention and their advantages are best understood by referring to FIGS. 1–6 of the drawings, like numerals being used for like and corresponding parts of the various drawings. All wire gauges referred to in this document are preferably measured by the Brown & Sharpe technique.

Figure 2:
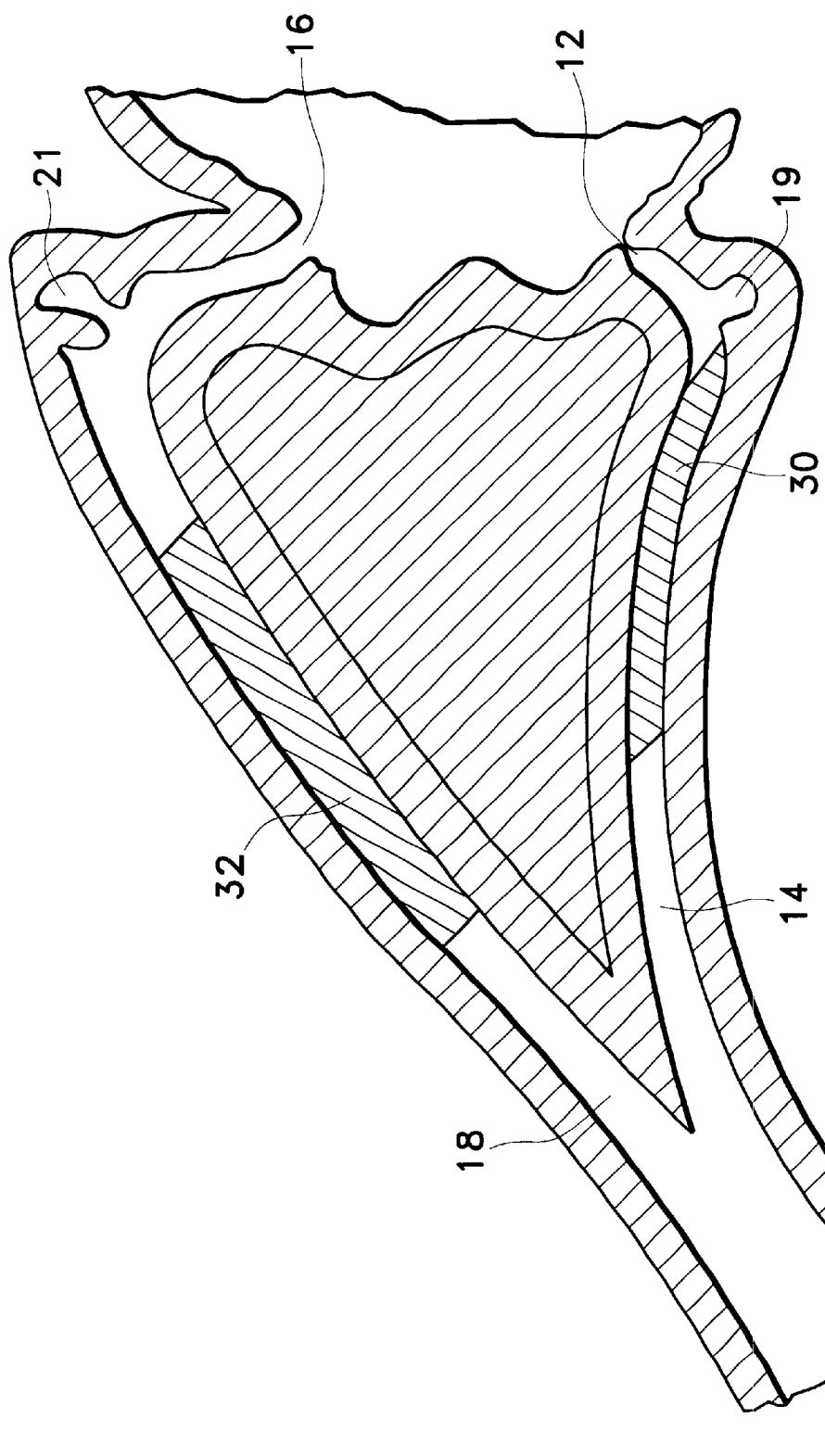
FIG. 2 is a schematic, front sectional view of the lacrimal canaliculi of FIG. 1 with the canaliculi blocked with conventional plugs.

FIG. 2 illustrates lacrimal canaliculi 14 and 18 blocked or occluded by plugs 30 and 32, respectively. Plugs 30 and 32 are preferably cast-in place thermoplastic plugs as disclosed in U.S. Pat. No. 5,469,867. Alternatively, plugs 30 and 32 may be any of the conventional water-insoluble plugs that are typically flushed down nasolacrimal duct 22. Although plugs 30 and 32 as shown in FIG. 2 totally block canaliculi 14 and 18, the plugs may be designed or formed so as to only partially block canaliculi 14 and 18, if desired. Plugs 30 and 32 may also be formed to extend into ampullae 19 and 21, if desired. Furthermore, reference numerals 30 and 32 may alternatively represent undesired obstructions in canaliculi 14 and 18, respectively.

Figure 3:
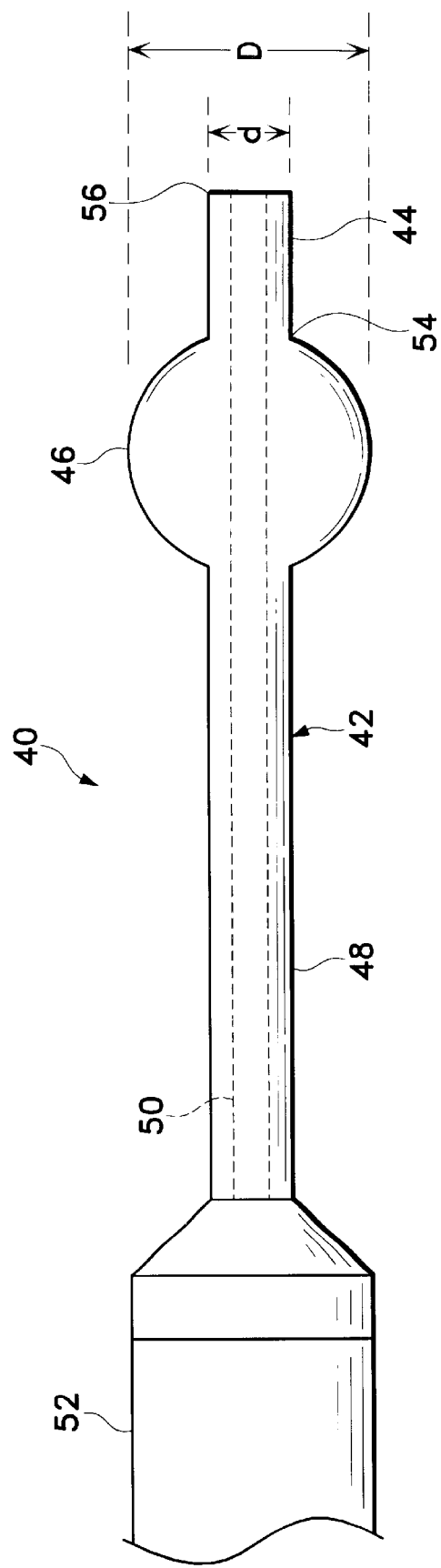
FIG. 3 is a schematic side view of a cannula according to a first preferred embodiment of the present invention.
Figure 6:
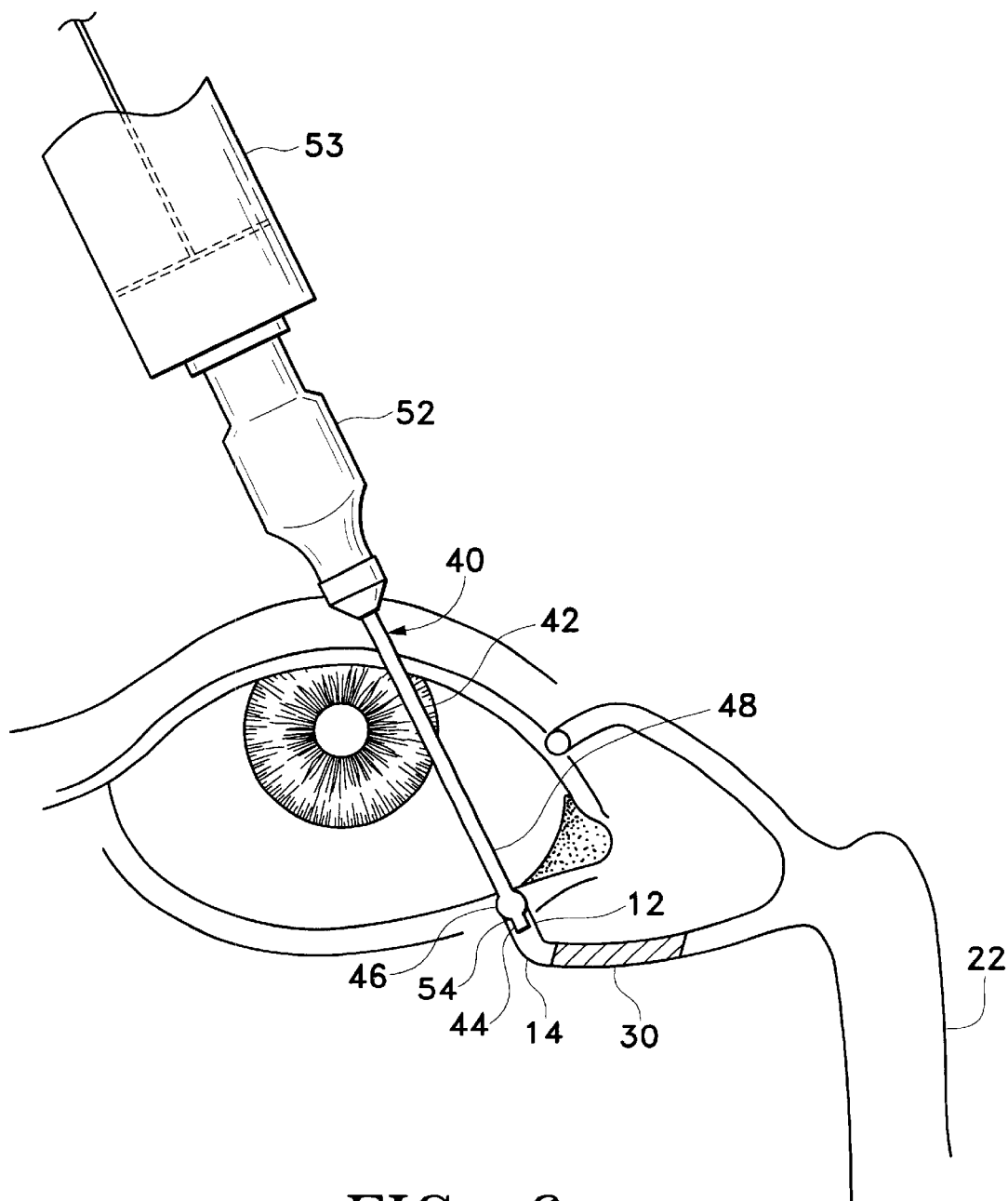
FIG. 6 is a schematic view of the cannula of FIG. 3 being used to remove a punctal plug from the lacrimal canaliculus.

Referring now to FIG. 3, a cannula 40 according to a first preferred embodiment of present invention is illustrated. Cannula 40 generally comprises a body 42 having a distal portion 44, an external annulus 46, a proximal portion 48, and a hollow bore 50 running within cannula 40 from distal portion 44 to proximal portion 48. Proximal portion 48 is coupled to a hub 52. Hub 52 is for removably coupling to a conventional syringe 53, as shown in FIG. 6. Cannula 40 is preferably made of an inert metal such as surgical stainless steel, although other conventional metals, plastics, synthetics or composite materials may also be utilized.

As shown in FIG. 3, external annulus 46 has a generally spherical geometry, with distal portion 44 of body 42 extending axially therefrom. External annulus 46 has a shoulder 54 located proximate distal portion 44. Preferably, shoulder 54 of external annulus 46 is located from about 0.5 mm to about 2.5 mm from a distal end 56 of distal portion 44. External annulus 46 has an outer diameter "D" substantially greater than an outer diameter "d" of distal portion 44. Preferably, the outer diameters are selected so that, when measured in inches, d<D<6d. For the human eye, distal portion 44 preferably has an outer diameter d from about 24 gauge to about 32 gauge, so that it can easily be inserted into puncta 12 and 16 without any dilation. For the human eye, external annulus 46 preferably has an outer diameter D of about 18 gauge to about 8 gauge, so that shoulder 54 forms a smooth surface for contact with the external surface of puncta 12 and 16. For the human eye, d is most preferably 27 gauge; and D is most preferably 16 gauge. Although in FIG. 3 proximal portion 48 is shown with an outer diameter identical to the outer diameter d of distal portion 44, proximal portion 48 may have a different diameter, if desired.

As shown best in FIG. 6, cannula 40 is especially suited for the removal of cast-in place thermoplastic plug 30 within canaliculus 14 in the following preferred manner. A warm, ophthalmic fluid such as saline solution is drawn into syringe 53 in the conventional manner. The ophthalmic fluid is preferably heated to above the melting point of the polymer or polymer composite comprising plug 30. Preferably, the ophthalmic fluid is heated to a temperature from about 3° C. to about 5° C. above the melting point of said polymer or polymer composite. Next, distal portion 44 is inserted into punctum 12 to the point where shoulder 54 of external annulus 46 is in contact with the external surface of punctum 12. The geometry of cannula 40 thus effectively seals punctum 12 without any dilation of punctum 12, and without the necessity of forcefully pressing cannula 40 against the punctal tissue to create a seal. In addition, due to the relatively short length of distal portion 44 (e.g. 0.5 mm to 2.5 mm), distal portion 44 can be easily inserted into canaliculus 14 without contacting plug 30 and thus interfering with the formation of the punctal seal. Next, the warm ophthalmic fluid is injected into canaliculus 14 via hollow bore 50 by actuating syringe 53. The warm ophthalmic fluid begins to soften the polymer or polymer composite material comprising plug 30. Simultaneously, the pressure within canaliculus 14 between plug 30 and shoulder 54 increases, and the canalicular tissue surrounding plug 30 gently expands away from plug 30. In this manner, plug 30 is quickly and easily dislodged from canaliculus 14. As additional, warm, ophthalmic fluid is injected, further softening of plug 30 occurs, and plug 30 is eventually flushed down nasolacrimal duct 22. During the entire flushing procedure, it is believed that plug 30 remains a flowable, viscous mass, rather than becoming dissolved into the warm ophthalmic fluid.

Figure 1:
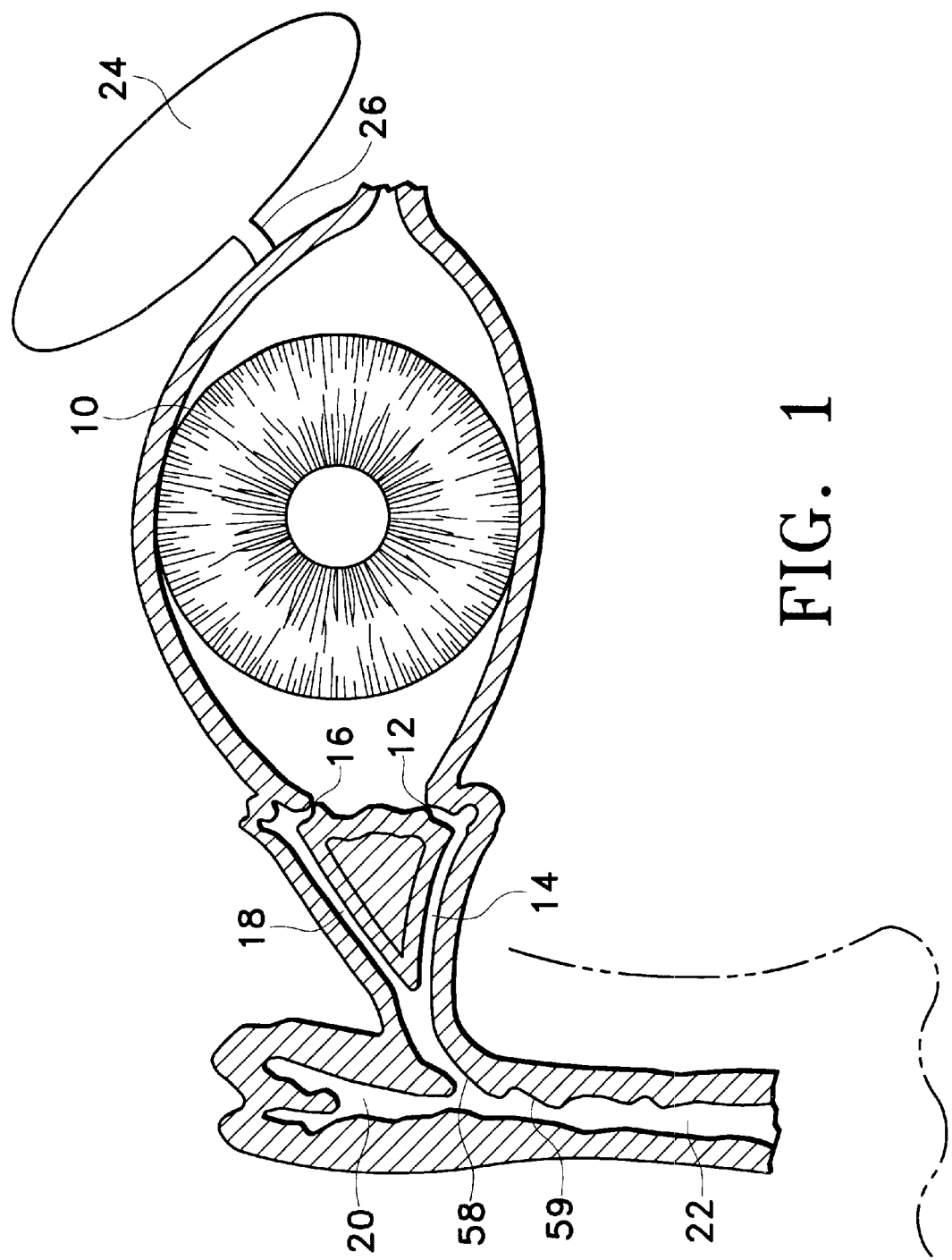
FIG. 1 is a schematic, front, partially sectional view of the lacrimal duct system of the mammalian eye.

It is also believed that the above-described softening of plug 30 via the warm ophthalmic fluid provides several additional advantages. First, plug 30 may be flushed at a lower pressure than conventional water-insoluble plugs. Second, after softening, plug 30 more easily negotiates turns 58 and surface irregularities 59 within canaliculus 14 or nasolacrimal duct 22, as shown in FIG. 1. Both of these advantages increase the chance of successfully flushing plug 30 and reduce the chance of over-pressurizing canaliculus 14.

If it is desired, a lipophilic compound such as a mineral oil or fatty acid ester may be used as the ophthalmic fluid in the above-described process instead of saline solution. Such lipophilic materials migrate into and diffuse within the polymer or polymer composite comprising plug 30 causing the plug 30 to have a lower melting point. Therefore, such lipophilic compounds reduce the degree of heating required of the ophthalmic fluid. Alternatively, if a sufficient amount of lipophilic compound is used to reduce the melting point of the polymer or polymer composite comprising plug 30, heating of the compound may not be required.

Cannula 40 may also be used to remove a conventional, water-insoluble plug 30, or an obstruction 30, within canaliculus 14 in the following preferred manner. An ophthalmic fluid such as saline solution is drawn into syringe 53 in the conventional manner. Next, distal portion 44 is inserted into punctum 12 to the point where shoulder 54 of external annulus 46 is in contact with the external surface of punctum 12. The geometry of cannula 40 thus effectively seals punctum 12 without any dilation of punctum 12, and without the necessity of forcefully pressing cannula 40 against the punctal tissue to create a seal. Next, the ophthalmic fluid is injected into canaliculus 14 via hollow bore 50 by actuating syringe 53. As more ophthalmic fluid is injected, the pressure within canaliculus 14 between plug 30 and shoulder 54 increases until the means for anchoring plug 30 within canaliculus 14, such as a collapsible flared section, is overcome. Additional saline is injected until plug 30 is flushed down nasolacrimal duct 22.

Figure 4:
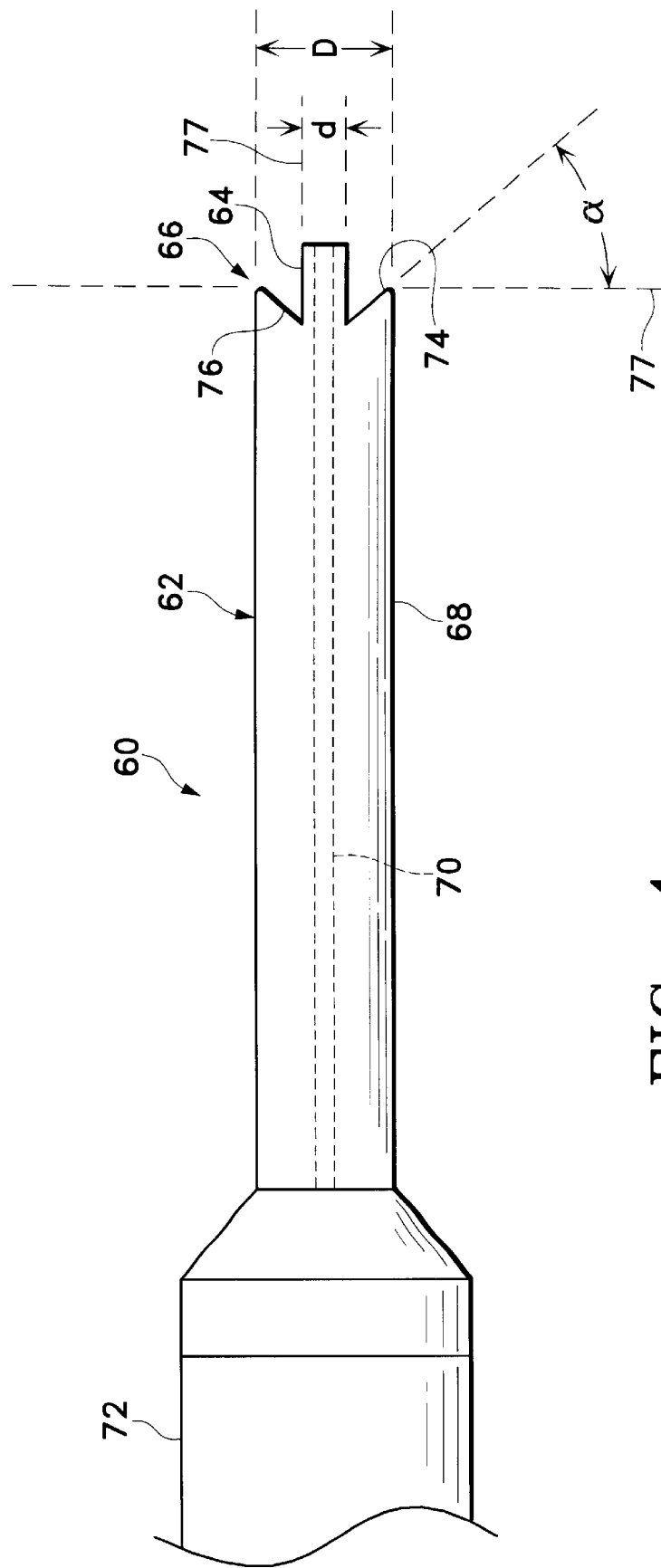
FIG. 4 is a schematic side view of a cannula according to a second preferred embodiment of the present invention.

Referring now to FIG. 4, a cannula 60 according to a second preferred embodiment of present invention is illustrated. Cannula 60 generally comprises a body 62 having a distal portion 64, an external annulus 66, a proximal portion 68, and a hollow bore 70 running within cannula 60 from distal portion 64 to proximal portion 68. Proximal portion 68 is coupled to a hub 72. Hub 72 is for removably coupling to a conventional syringe 53. Cannula 60 is preferably made of the same materials as cannula 40. Preferably, distal portion 64 has a length of about 0.5 mm to about 2.5 mm.

As shown in FIG. 4, external annulus 66 has a generally inverted-cone shaped geometry, with distal portion 64 of body 62 extending axially from the tip toward the base of the cone. More specifically, external annulus 66 has a rounded shoulder 74 proximate the base of its inverted-cone shaped geometry, and a slanted wall 76 that forms the wall of the inverted cone. For the human eye, slanted wall 76 preferably forms an angle $\alpha$ from about 10 degrees to about 80 degrees with a line 77 running perpendicular to the longitudinal axis of cannula 60. For the human eye, distal portion 64 preferably has an outer diameter d from about 24 gauge to about 32 gauge, so that it can easily be inserted into puncta 12 and 16 without any dilation. For the human eye, external annulus 66 preferably has an outer diameter D of about 18 gauge to about 8 gauge, so that shoulder 74 and slanted wall 76 form a smooth surface for contact with the external surface of puncta 12 and 16. For the human eye, d is most preferably 27 gauge, D is most preferably 16 gauge, and angle $\alpha$ is most preferably about 30 to about 60 degrees. External annulus 66 thus has a geometry specifically designed for engaging and sealing puncta 12 and 16.

Cannula 60 is especially suited for the removal of cast-in place thermoplastic plug 30 within canaliculus 14 in the following preferred manner, which is substantially similar to, and has the same advantages of, the manner described above for cannula 40. A warm, ophthalmic fluid such as saline solution is drawn into syringe 53 in the conventional manner. The ophthalmic fluid is preferably heated to above the melting point of the polymer or polymer composite comprising plug 30. Preferably, the ophthalmic fluid is heated to a temperature from about 3° C. to about 5° C. above the melting point of said polymer or polymer composite. Next, distal portion 64 is inserted into punctum 12 to the point where rounded shoulder 74 and slanted wall 76 of external annulus 66 are in contact with the external surface of punctum 12. The geometry of cannula 60 thus effectively seals punctum 12 without any dilation of punctum 12, and without the necessity of forcefully pressing cannula 60 against the punctal tissue to create a seal. In addition, due to the relatively short length of distal portion 64 (e.g. 0.5 mm to 2.5 mm), distal portion 64 can be easily inserted into canaliculus 14 without contacting plug 30 and thus interfering with the formation of the punctal seal. Next, the warm ophthalmic fluid is injected into canaliculus 14 via hollow bore 70 by actuating syringe 53. The warm ophthalmic fluid begins to soften the polymer or polymer composite material comprising plug 30. Simultaneously, the pressure within canaliculus 14 between plug 30 and punctum 12 increases, and the canalicular tissue surrounding plug 30 gently expands away from plug 30. In this manner, plug 30 is quickly and easily dislodged from canaliculus 14. As additional, warm, ophthalmic fluid is injected, further softening of plug 30 occurs, and plug 30 is eventually flushed down nasolacrimal duct 22. If it is desired, a lipophilic compound such as a mineral oil or fatty acid ester may be used as the ophthalmic fluid instead of saline solution, as described above in connection with cannula 40.

Cannula 60 may also be used to remove a conventional, water-insoluble plug 30, or an obstruction 30, within canaliculus 14 the following preferred manner, which is substantially similar to, and has the same advantages of, the manner described above for cannula 40. An ophthalmic fluid such saline solution is drawn into syringe 53 in the conventional manner. Next, distal portion 64 is placed within punctum 12 to the point where rounded shoulder 74 and slanted wall 76 of external annulus 66 are in contact with the external surface of punctum 12. The geometry of cannula 60 thus effectively seals punctum 12 without any dilation of punctum 12, and without the necessity of forcefully pressing cannula 60 against the punctal tissue to create a seal. Next, the ophthalmic fluid is injected into canaliculus 14 via hollow bore 70 by actuating syringe 53. As more ophthalmic fluid is injected, the pressure within canaliculus 14 between plug 30 and punctum 12 increases until the means for anchoring plug 30 within canaliculus 14 is overcome. Additional saline is injected until plug 30 is flushed down nasolacrimal duct 22.

Figure 5:
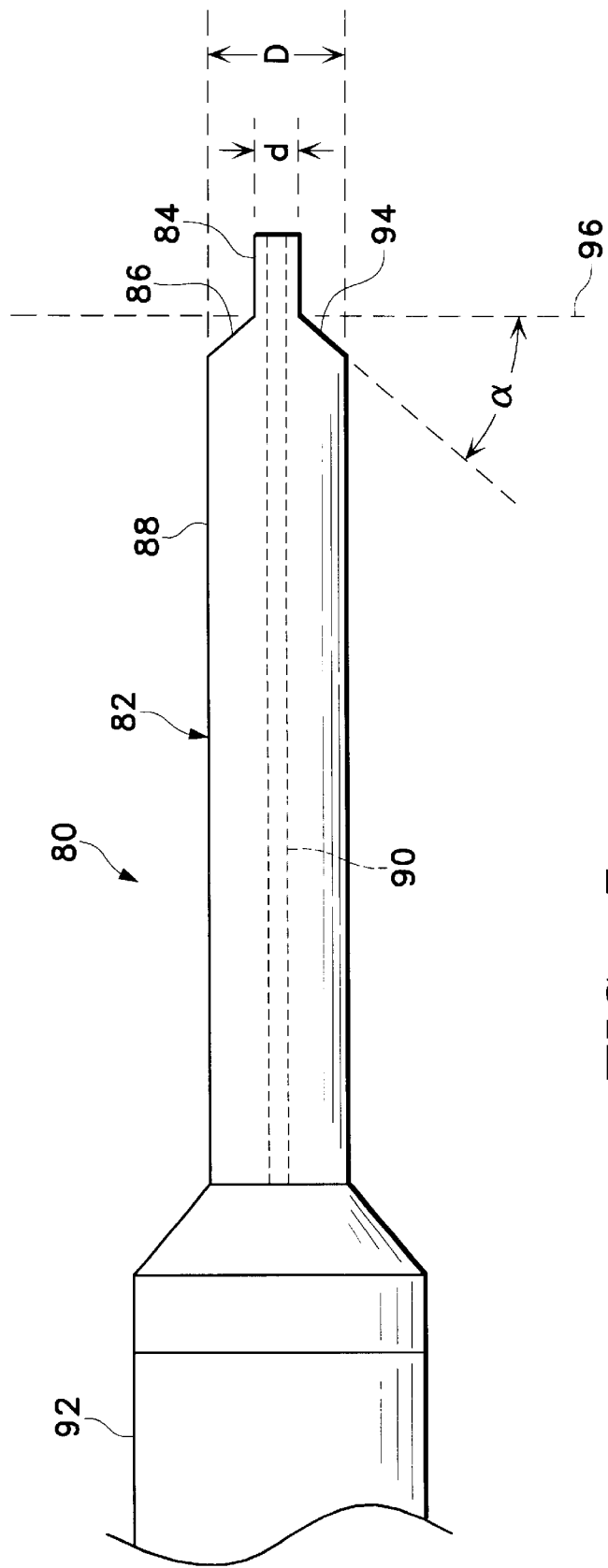
FIG. 5 is a schematic side view of a cannula according to a third preferred embodiment of the present invention.

Referring now to FIG. 5, a cannula 80 according to a third preferred embodiment of present invention is illustrated. Cannula 80 generally comprises a body 82 having a distal portion 84, an external annulus 86, a proximal portion 88, and a hollow bore 90 running within cannula 80 from distal portion 84 to proximal portion 88. Proximal portion 88 is coupled to a hub 92. Hub 92 is for removably coupling to a conventional syringe 53. Cannula 80 is preferably made of the same materials as cannula 40. Preferably, distal portion 84 has a length of about 0.5 mm to about 2.5 mm.

As shown in FIG. 5, external annulus 86 has a generally cone shaped geometry, with distal portion 84 of body 82 extending axially and outwardly from the tip of the cone. More specifically, external annulus 86 has a slanted wall 94 that forms the wall of the cone. For the human eye, slanted wall 94 preferably forms an angle $\alpha$ from about 5 degrees to about 30 degrees from a line 96 running perpendicular to the longitudinal axis of cannula 80. For the human eye, distal portion 84 preferably has an outer diameter d from about 24 gauge to about 32 gauge, so that it can easily be inserted into puncta 12 and 16 without any dilation. For the human eye, proximal portion 88 preferably has an outer diameter D of about 18 gauge to about 8 gauge, so that slanted wall 94 forms a smooth surface for contact with the external surface of puncta 12 and 16. For the human eye, d is most preferably 27.gauge, D is most preferably 16 gauge, and angle $\alpha$ of slanted wall 94 is most preferably about 5 to about 20 degrees.

Cannula 80 is especially suited for the removal of cast-in place thermoplastic plug 30 within canaliculus 14 in the following preferred manner, which is substantially similar to, and has the same advantages of, the manner described above for cannula 40. A warm, ophthalmic fluid such as saline solution is drawn into syringe 53 in the conventional manner. The ophthalmic fluid is preferably heated to above the melting point of the polymer or polymer composite comprising plug 30. Preferably, the ophthalmic fluid is heated to a temperature from about 3° C. to about 5° C. above the melting point of said polymer or polymer composite. Next, distal portion 84 is inserted into punctum 12 to the point where slanted wall 94 of external annulus 46 contacts the external surface of punctum 12. Due to the sharpness of angle α with respect to the longitudinal axis of cannula 80, slanted wall 94 effectively seals punctum 12 without any dilation of punctum 12, and without the necessity of forcefully pressing cannula 80 against the punctal tissue to create a seal. In addition, due to the relatively short length of distal portion 84 (e.g. 0.5 mm to 2.5 mm), distal portion 84 can be easily inserted into canaliculus 14 without contacting plug 30 and thus interfering with the formation of the punctal seal. Next, the warm ophthalmic fluid is injected into canaliculus 14 via hollow bore 90 by actuating syringe 53. The warm ophthalmic fluid begins to soften the polymer or polymer composite material comprising plug 30. Simultaneously, the pressure within canaliculus 14 between plug 30 and slanted wall 94 increases, and the canalicular tissue surrounding plug 30 gently expands away from plug 30. In this manner, plug 30 is quickly and easily dislodged from canaliculus 14. As additional, warm, ophthalmic fluid is injected, further softening of plug 30 occurs, and plug 30 is eventually flushed down nasolacrimal duct 22. If it is desired, a lipophilic compound such as a mineral oil or fatty acid ester may be used as the ophthalmic fluid instead of saline solution, as described above in connection with cannula 40.

Cannula 80 may also be used to remove a conventional, water-insoluble plug 30, or an obstruction 30, within canaliculus 14 in the following preferred manner, which is substantially similar to, and has the same advantages of, the manner described above for cannula 40. An ophthalmic fluid such as saline solution is drawn into syringe 53 in the conventional manner. Next, distal portion 84 is inserted into punctum 12 to the point slanted wall 94 of external annulus 86 contacts the external surface of punctum 12. Due to the sharpness of angle α with respect to the longitudinal axis of cannula 80, slanted wall 94 effectively seals punctum 12 without any dilation of punctum 12, and without the necessity of forcefully pressing cannula 80 against the punctal tissue to create a seal. Next, the ophthalmic fluid is injected into canaliculus 14 via hollow bore 90 by actuating syringe 53. As more ophthalmic fluid is injected, the pressure within canaliculus 14 between plug 30 and slanted wall 94 increases until the means for anchoring plug 30 within canaliculus 14 is overcome. Additional saline is injected until plug 30 is flushed down nasolacrimal duct 22.

From the above, it may be appreciated that the present invention provides an improved cannula for the removal of punctal plugs that are used to treat dry eye syndrome, and for the removal of obstructions in the lacrimal canaliculi. The improved cannula is easy to use, safe for the patient, and capable of economic manufacture. Significantly, the cannula can be used to remove such plugs or obstructions without any dilation, or with minimal dilation, of the punctum, and without the necessity of forcefully pressing the cannula against the punctal tissue to create a seal.

The present invention is illustrated herein by example, and various modifications may be made by a person of ordinary skill in the art. For example, although the cannula of the present invention has been described above in connection with the removal of punctal plugs or obstructions in lower canaliculus 14, it of course may also be used to remove plugs or obstructions in upper canaliculus 18, or in other body channels or ducts having similar puncta.

It is believed that the operation and construction of the present invention will be apparent from the foregoing description. While the apparatus, method, and compositions shown or described above have been characterized as being preferred, various changes and modifications may be made therein without departing from the spirit and scope of the invention as defined in the following claims.

What is claimed is:

1. A cannula, comprising:
   a body having a distal portion, an external annulus disposed proximate said distal portion, and a hollow bore for fluid delivery from said distal portion;
   said distal portion being capable of insertion into a mammalian punctum without dilating said punctum; and
   said external annulus having a geometry capable of forming a seal with an external surface of said punctum without dilating said punctum.

2. The cannula of claim 1 further comprising a proximal portion coupled to a hub, and wherein said hub is adapted to be removably coupled to a syringe.

3. The cannula of claim wherein said distal portion has a length of about 0.5 mm to about 2.5 mm.

4. The cannula of claim 1 wherein said external annulus has an outer diameter greater than an outer diameter of said distal portion.

5. The cannula of claim wherein said distal portion extends axially from said external annulus.

6. The cannula of claim 1 wherein said external annulus has a shoulder forming a smooth surface for contacting said external surface of said punctum.

7. A method of dislodging a plug or an obstruction from a mammalian canaliculus, said canaliculus having a punctum, said method comprising the steps of:
   providing a cannula comprising a body having a distal portion, an external annulus disposed proximate said distal portion, and a hollow bore for fluid delivery from said distal portion;
   inserting said distal portion into said punctum without dilating said punctum;
   sealing said punctum by contacting an external surface of said punctum with said external annulus without dilating said punctum; and
   injecting an ophthalmic fluid into said punctum with said cannula to pressurize a portion of said canaliculus between said plug or obstruction and said punctum.

8. The method of claim 7 wherein said sealing step is performed without forcefully pressing said cannula against said external surface of said punctum.

9. The method of claim 7 wherein said cannula in said providing step includes a proximal portion coupled to a hub, and wherein said hub is adapted to be removably coupled to a syringe.

10. The method of claim 7 wherein said distal portion has a length of about 0.5 mm to about 2.5 mm.

11. The method of claim 7 wherein said providing step comprises providing said external annulus with an outer diameter greater than an outer diameter of said distal portion, and wherein said distal portion extends axially from said external annulus.

12. The method of claim 7 wherein said providing step comprises providing said external annulus with a shoulder forming a smooth surface for contacting said external surface of said punctum.

13. The method of claim 7 wherein said ophthalmic fluid is a saline solution.

14. The method of claim 7 wherein said ophthalmic fluid is a lipophilic compound.

15. A lacrimal cannula, comprising:
   a body having a distal portion, an external annulus, and a hollow bore for fluid delivery from said distal portion;
   said external annulus having a generally spherical geometry with said distal portion extending axially therefrom;
   said distal portion being capable of insertion into a mammalian lacrimal punctum without dilating said punctum; and
   said external annulus being capable of forming a seal with an external surface of said punctum without dilating said punctum.

16. The lacrimal cannula of claim 15 wherein an outer diameter of said external annulus is greater than an outer diameter of said distal portion.

17. The lacrimal cannula of claim 16 wherein said outer diameter of said external annulus is less than six times said outer diameter of said distal portion.

18. The lacrimal cannula of claim 16 wherein said outer diameter of said external annulus is from about 18 gauge to about 8 gauge, and said outer diameter of said distal portion is from about 24 gauge to about 32 gauge.

19. The lacrimal cannula of claim 15 further comprising a proximal portion coupled to a hub, and wherein said hub is adapted to be removably coupled to a syringe.

20. The lacrimal cannula of claim 15 wherein said distal portion has a length of about 0.5 mm to about 2.5 mm.

21. The lacrimal cannula of claim 15 wherein said external annulus has a smooth shoulder for contacting said external surface of said punctum.

22. A lacrimal cannula, comprising:
   a body having a distal portion, an external annulus, and a hollow bore for fluid delivery from said distal portion;
   said external annulus having a generally inverted-cone shape geometry with said distal portion extending axially from a tip toward a base of said cone;
   said distal portion being capable of insertion into a mammalian lacrimal punctum without dilating said punctum; and
   said external annulus being capable of forming a seal with an external surface of said punctum without dilating said punctum.

23. The lacrimal cannula of claim 22 wherein an outer diameter of said external annulus is greater than an outer diameter of said distal portion.

24. The lacrimal cannula of claim 23 wherein said outer diameter of said external annulus is from about 18 gauge to about 8 gauge, and said outer diameter of said distal portion is from about 24 gauge to about 32 gauge.

25. The lacrimal cannula of claim 22 further comprising a proximal portion coupled to a hub, and wherein said hub is adapted to be removably coupled to a syringe.

26. The lacrimal cannula of claim 22 wherein said distal portion has a length of about 0.5 mm to about 2.5 mm.

27. The lacrimal cannula of claim 22 wherein said external annulus comprises:
   a rounded shoulder proximate said base of said cone;
   a slanted wall forming a wall of said cone;
   wherein said rounded shoulder and said slanted wall are adapted to contact said external surface of said punctum.

28. A lacrimal cannula, comprising:
   a body having a distal portion, an external annulus, and a hollow bore for fluid delivery from said distal portion;
   said external annulus having a generally cone shape geometry with said distal portion extending axially and outwardly from a tip of said cone;
   said distal portion being capable of insertion into a mammalian lacrimal punctum without dilating said punctum; and
   said external annulus being capable of forming a seal with an external surface of said punctum without dilating said punctum.

29. The lacrimal cannula of claim 28 wherein an outer diameter of said external annulus is greater than an outer diameter of said distal portion.

30. The lacrimal cannula of claim 29 wherein said outer diameter of said external annulus is from about 18 gauge to about 8 gauge, and said outer diameter of said distal portion is from about 24 gauge to about 32 gauge.

31. The lacrimal cannula of claim 28 further comprising a proximal portion coupled to a hub, and wherein said hub is adapted to be removably coupled to a syringe.

32. The lacrimal cannula of claim 28 wherein said distal portion has a length of about 0.5 mm to about 2.5 mm.

33. The lacrimal cannula of claim 28 wherein said external annulus comprises a slanted wall forming a wall of said cone for contacting said external surface of said punctum.

34. The lacrimal cannula of claim 33 wherein said slanted wall forms an angle from about 5 degrees to about 30 degrees from a line disposed perpendicular to a longitudinal axis of said cannula.

35. A method of removing a cast-in place thermoplastic plug from a mammalian lacrimal canaliculus, said canaliculus having a punctum, said method comprising the steps of:
   providing a cannula comprising a body having a distal portion, an external annulus, and a hollow bore for fluid delivery from said distal portion, said distal portion extending axially from said external annulus;
   inserting said distal portion into said punctum without dilating said punctum;
   sealing said punctum by contacting an external surface of said punctum with said external annulus without dilating said punctum; and
   injecting a warm ophthalmic fluid into said punctum with said cannula to pressurize a portion of said canaliculus between said cast-in place thermoplastic plug and said punctum to dislodge said plug.

36. The method of claim 35 wherein said injecting step further comprises:
   softening said cast-in place thermoplastic plug with said warm ophthalmic fluid; and
   gently expanding a portion of said canaliculus surrounding said plug.

37. The method of claim 35 further comprising the step of injecting an additional amount of said warm ophthalmic fluid, after said plug is dislodged from said canaliculus, to flush said plug down a nasolacrimal duct.

38. The method of claim 35 wherein said sealing step is performed without forcefully pressing said cannula against said external surface of said punctum.

39. The method of claim 35 wherein said cannula in said providing step includes a proximal portion coupled to a hub, and wherein said hub is adapted to be removably coupled to a syringe.

40. The method of claim 35 wherein said distal portion has a length of about 0.5 mm to about 2.5 mm.

41. The method of claim 35 wherein said providing step comprises providing said external annulus with an outer diameter greater than an outer diameter of said distal portion.

42. The method of claim 35 wherein said providing step comprises providing said external annulus with a wall forming a smooth surface for contacting said external surface of said punctum.

43. The method of claim 35 wherein said providing step comprises providing said external annulus with a generally spherical geometry.

44. The method of claim 35 wherein said providing step comprises providing said external annulus with a generally inverted-cone shaped geometry.

45. The method of claim 35 wherein said providing step comprises providing said external annulus with a generally cone shaped geometry.

46. The method of claim 35 wherein:

said cast-in place thermoplastic plug comprises a polymer or polymer composite; and said warm ophthalmic fluid is heated from about 3° C. to about 5° C. above a melting point of said polymer or polymer composite.

47. The method of claim 35 wherein said warm ophthalmic fluid is a saline solution.

48. The method of claim 35 wherein said warm ophthalmic fluid is a lipophilic compound.

* * * * *

UNITED STATES PATENT AND TRADEMARK OFFICE
CERTIFICATE OF CORRECTION

PATENT NO.    : 6,428,502 B1
DATED         : August 6, 2002
INVENTOR(S)   : Lang, John C.

It is certified that error appears in the above-identified patent and that said Letters Patent is hereby corrected as shown below:

<u>Column 8,</u>
Line 60, delete "." after "27" and delete the bold font on "27".

<u>Column 10,</u>
Line 25, insert -- 1 -- after "claim".
Line 30, insert -- 1 -- after "claim".

Signed and Sealed this

Seventeenth Day of December, 2002

JAMES E. ROGAN
*Director of the United States Patent and Trademark Office*